(12) United States Patent
Lichtenstein et al.

(10) Patent No.: US 10,596,349 B2
(45) Date of Patent: Mar. 24, 2020

(54) CATHETER CLIPS

(71) Applicant: BIOSENSE WEBSTER (ISRAEL) LTD., Yokneam (IL)

(72) Inventors: Yoav Lichtenstein, Raanana (IL); Roy Urman, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 547 days.

(21) Appl. No.: 14/597,382

(22) Filed: Jan. 15, 2015

(65) Prior Publication Data

US 2015/0217087 A1 Aug. 6, 2015

Related U.S. Application Data

(60) Provisional application No. 61/935,932, filed on Feb. 5, 2014.

(51) Int. Cl.
| | |
|---|---|
| *A61M 25/01* | (2006.01) |
| *A61M 25/02* | (2006.01) |
| *A61B 90/57* | (2016.01) |
| *A61B 90/50* | (2016.01) |
| *A61B 17/00* | (2006.01) |

(52) U.S. Cl.
CPC ......... *A61M 25/0102* (2013.01); *A61B 90/50* (2016.02); *A61B 90/57* (2016.02);
(Continued)

(58) Field of Classification Search
CPC ........ A61M 25/0102; A61M 2025/024; A61M 25/02; A61M 5/44; A61M 29/02;
(Continued)

(56) References Cited

U.S. PATENT DOCUMENTS

| | | | |
|---|---|---|---|
| 4,986,815 | A | 1/1991 | Schneider |
| 5,405,110 | A | 4/1995 | Mistretta |
| | | (Continued) | |

FOREIGN PATENT DOCUMENTS

| | | |
|---|---|---|
| JP | 3009426 U | 4/1995 |
| JP | 3-251259 | 1/2002 |
| JP | 2008502429 | 1/2008 |

OTHER PUBLICATIONS

European Search Report dated Jul. 29, 2015 for corresponding Application No. EP15153765.1.
(Continued)

*Primary Examiner* — Kathleen S Holwerda
*Assistant Examiner* — Brooke Labranche
(74) *Attorney, Agent, or Firm* — Louis J. Capezzuto

(57) ABSTRACT

A device for gripping a catheter, including a first jaw having a first exterior side and a first radial passage. The device has a second jaw having a second exterior side, opposite the first exterior side, and a second radial passage. The device also has a resilient joint connecting the first and second jaws so that manual compression of the first exterior side toward the second exterior side causes relative rotation between the first and second jaws that mutually aligns the first and second radial passages, such that the catheter can be inserted through the first and second radial passages, and so that releasing the manual compression causes the first and second jaws to rotate so that the first and second radial passages are no longer mutually aligned and so that the catheter passes through and is gripped by the device along mutually aligned first and second central axes.

22 Claims, 5 Drawing Sheets

(52) U.S. Cl.
CPC ... *A61M 25/02* (2013.01); *A61B 2017/00469* (2013.01); *A61M 2025/024* (2013.01)

(58) Field of Classification Search
CPC .... A61M 2025/0293; A61M 25/09041; A61M 39/28; A61M 25/01; A61M 25/013; Y10T 24/3984; A61F 2/0063; A61B 90/50; A61B 90/57; A61B 17/0487; A61B 17/1227; A61B 17/083
See application file for complete search history.

(56) References Cited

U.S. PATENT DOCUMENTS

| | | | |
|---|---|---|---|
| 6,305,053 B1* | 10/2001 | Galbreath | F16G 11/101 24/115 G |
| 7,415,750 B2* | 8/2008 | Kinebuchi | F16G 11/101 24/115 G |
| 7,628,783 B2 | 12/2009 | McDaniel | |
| 2002/0151871 A1 | 10/2002 | Gaiser et al. | |
| 2005/0096688 A1 | 5/2005 | Slazas et al. | |
| 2005/0277909 A1 | 12/2005 | McDaniel | |
| 2010/0145280 A1 | 6/2010 | Daniels, Jr. et al. | |
| 2011/0138526 A1* | 6/2011 | Hsu | E03D 9/03 4/223 |
| 2012/0116357 A1 | 5/2012 | Hakky et al. | |
| 2013/0096505 A1 | 4/2013 | Urmey | |

OTHER PUBLICATIONS

U.S. Appl. No. 61/935,932, filed Feb. 5, 2014.
JP2015-019971- English translation of Examination Report dated Oct. 16, 2018.

* cited by examiner

CATHETER CLIPS

CROSS-REFERENCE TO RELATED APPLICATION

This application claims the benefit of U.S. Provisional Patent Application 61/935,932, filed Feb. 5, 2014, which is incorporated herein by reference.

FIELD OF THE INVENTION

The present invention relates generally to a catheter, and specifically to facilitating rotation and translation of the catheter while the catheter is inserted into a patient.

BACKGROUND OF THE INVENTION

It is advantageous that catheters have as small a diameter as possible, in order to reduce the trauma to a patient into whom the catheter is inserted. Such catheters may be difficult for a physician using the catheter to manipulate.

Methods for manipulating a catheter, such as the narrow diameter catheter referred to above, are known in the art. For example, U.S. patent application Ser. No. 2005/0096688, to Slazas et al., whose disclosure is incorporated herein by reference, describes a gripper for a catheter shaft which is a flexible tube that surrounds a portion of the shaft. A physician can move the gripper to a selected position on the catheter shaft, and then squeeze the outer surfaces of the gripper, which resiliently collapses around the catheter shaft. When squeezed, an inner surface of the gripper contacts the catheter shaft and can transmit forces applied by the physician to the outside of the gripper, including rotating of the catheter shaft or longitudinal pushing or pulling.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a device for gripping a catheter, the device including:

a first jaw having a first grip surface on a first exterior side of the device and containing a first radial passage extending through the first jaw between a first central axis of the first jaw and a first exit point on an outer surface of the device;

a second jaw having a second grip surface on a second exterior side of the device, opposite to the first exterior side, and containing a second radial passage extending through the second jaw between a second central axis of the second jaw and a second exit point on the outer surface of the device; and a resilient joint connecting the first and second jaws so that manual compression of the first exterior side toward the second exterior side causes a relative rotation between the first and second jaws that mutually aligns the first and second radial passages and the first and second exit points, such that the catheter can be inserted through the first and second radial passages to the first and second central axes, and so that releasing the manual compression causes the first and second jaws to rotate so that the first and second radial passages are no longer mutually aligned while the first and second central axes are in mutual alignment, and so that the catheter passes through and is gripped by the device along the mutually aligned first and second central axes.

Typically, the first jaw includes a first plurality of first jaw leaves, and the second jaw includes a second plurality of second jaw leaves which interleave with the first jaw leaves.

In a disclosed embodiment the first and second jaws have identical geometric forms.

In a further disclosed embodiment the first grip surface includes a first set of ridges and indentations, and the second grip surface includes a second set of ridges and indentations. Typically, the first set and the second set align in a region in proximity to the first exit point and the second exit point on release of the manual compression.

The first jaw, the second jaw, and the resilient joint connecting the jaws may form a catheter grip, the device may further include a cradle which is configured to receive the catheter grip. Typically, the cradle includes a pawl which is configured to engage with the indentations so as to lock the catheter grip in place in the cradle.

In a yet further disclosed embodiment release of the manual compression causes the device to form an opening having an axis of symmetry corresponding to the mutually aligned first and second central axes, and the opening has a diameter configured to grip the catheter.

In an alternative embodiment the catheter has a catheter diameter, and release of the manual compression causes the first and second exterior sides to form a curved surface having a diameter at least 15 times greater than the catheter diameter.

There is further provided, according to an embodiment of the present invention, a method for gripping a catheter, including:

providing a first jaw having a first grip surface on a first exterior side of the first jaw and containing a first radial passage extending through the first jaw between a first central axis of the first jaw and a first exit point on an outer surface of the first jaw;

providing a second jaw having a second grip surface on a second exterior side of the second jaw, opposite to the first exterior side, and containing a second radial passage extending through the second jaw between a second central axis of the second jaw and a second exit point on an outer surface of the second jaw; and connecting the first and second jaws with a resilient joint so that manual compression of the first exterior side toward the second exterior side causes a relative rotation between the first and second jaws that mutually aligns the first and second radial passages and the first and second exit points, such that the catheter can be inserted through the first and second radial passages to the first and second central axes, and so that releasing the manual compression causes the first and second jaws to rotate so that the first and second radial passages are no longer mutually aligned while the first and second central axes are in mutual alignment, and so that the catheter passes through and is gripped by the first and second jaws along the mutually aligned first and second central axes.

The present disclosure will be more fully understood from the following detailed description of the embodiments thereof, taken together with the drawings, in which:

DETAILED DESCRIPTION OF EMBODIMENTS

Overview

It is advantageous that a catheter that is inserted into a patient during a medical procedure has a diameter that is as small as possible, to reduce trauma to the patient. However, the small diameter of the catheter, together with its length which is typically of the order of 1 meter, determines that the catheter is inherently flexible. While the flexibility may be an advantage, allowing, for example, the catheter to be inserted into a non-linear lumen, the small diameter of the catheter and its relatively long length typically makes the catheter difficult to manipulate.

Embodiments of the present invention facilitate the manipulation by providing a physician manipulating the catheter with a device that grips the catheter and which has a large mechanical advantage. A disclosed embodiment uses a pair of jaws, typically multi-ridged interleaved jaws, connected by a resilient joint such as a spring, as a catheter grip. Manual compression of the jaws aligns passages in the jaws so that a catheter can be inserted into a central region of the jaws. Releasing the manual compression, so that the spring of the grip returns to a "rest" condition, puts the grip into a relaxed state, herein also termed a grip uncompressed state, which is configured to automatically grasp the catheter.

An external diameter of the grip is considerably larger than the small diameter of the catheter, providing a mechanical advantage to the physician corresponding to the ratio of the two diameters. Consequently, in the grip relaxed-state virtually no effort is required by a physician in holding the catheter, and the relaxed-state grip may be easily grasped by the physician, enabling the physician to rotate and/or translate the catheter with very little effort.

In its relaxed-state the grip may be inserted into a free-standing cradle, relieving the physician of the need to hold the grip or the catheter. In its relaxed state the multiple ridges of the interleaved elements may be configured to align, forming ridges and intermediary indentations across the grip. A spring-loaded stopper may be attached to the cradle, so that, in a pawl-like manner, while the grip is in the cradle the stopper is able to engage with the aligned ridges and indentations of the grip. Alternatively, other indentations may be configured in the grip, and the stopper may be configured to engage with these indentations.

Typically, the free-standing cradle is attached to an adjustable arm, usually an articulated arm, which enables the cradle to be located in any orientation and/or location that is suitable for accepting the grip. The combination of the adjustable arm together with spring-loaded stopper, enables adjustments to made to orientation and location of the grip, and thus to the orientation and location of the catheter. Once the adjustments have been made, the stopper may engage with the indentations referred to above in order to lock the grip and the catheter in place.

DETAILED DESCRIPTION

Figure 1:
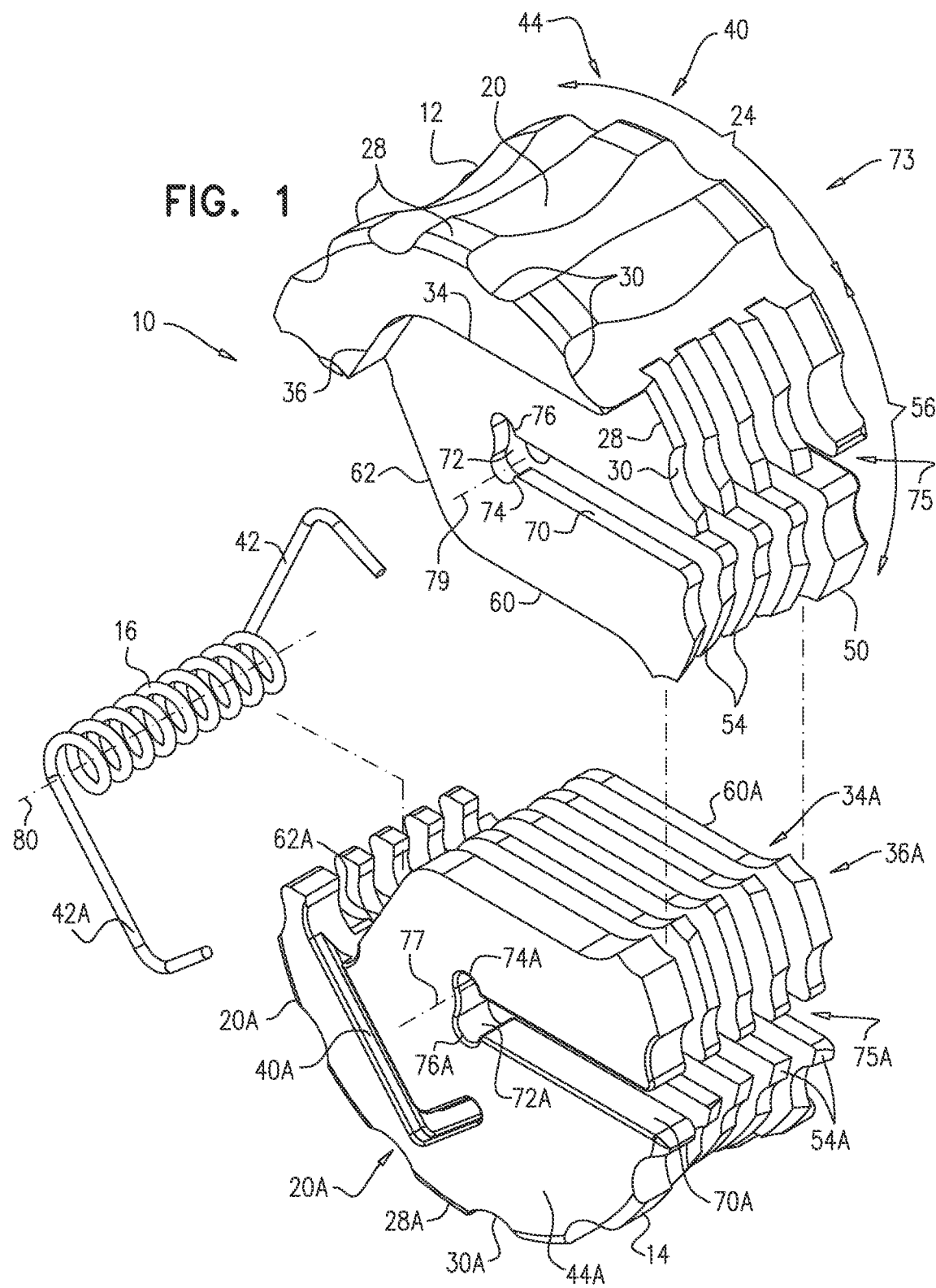
FIG. 1 is a schematic exploded view of a catheter device, according to an embodiment of the present invention.
Figure 2:
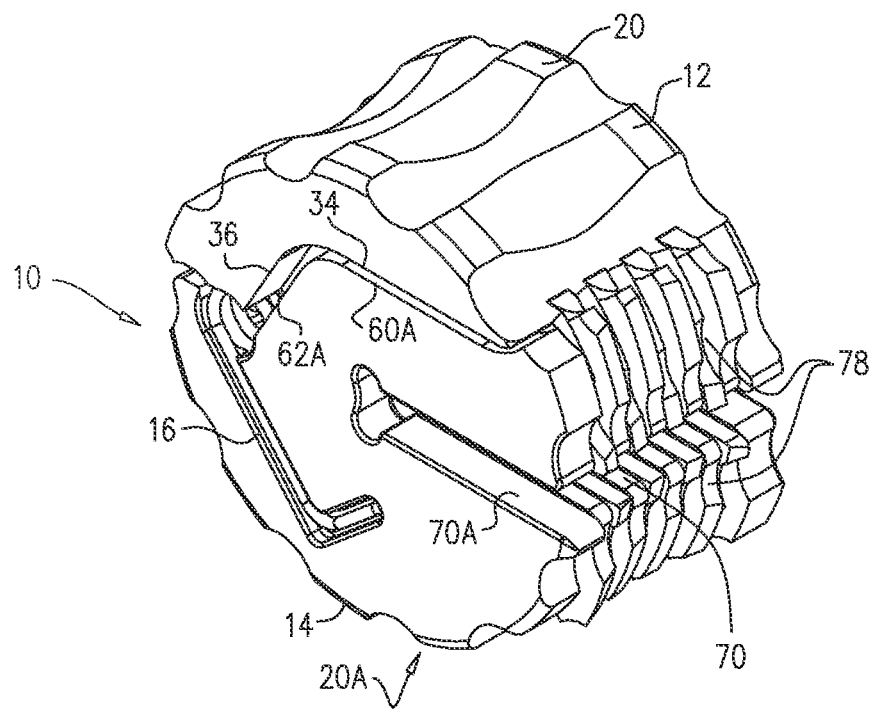
FIG. 2 is a schematic view of the assembled device in an open state, according to an embodiment of the present invention.
Figure 3:
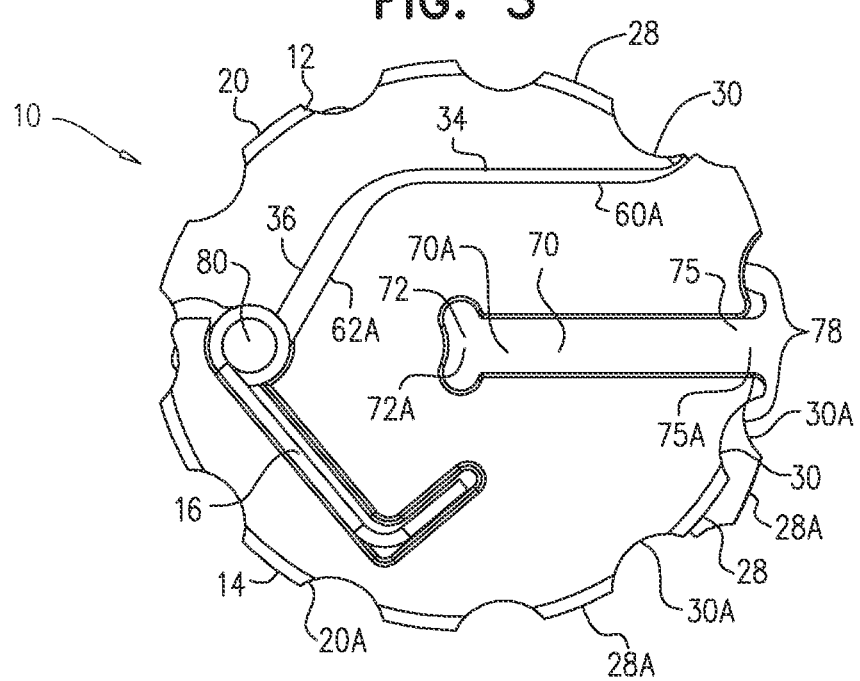
FIG. 3 is another schematic view of the assembled device in the open state, according to an embodiment of the present invention.

FIG. 1 is a schematic exploded view of a catheter device 10, FIG. 2 is a schematic view of the assembled device in an open state, and FIG. 3 is another schematic view of the assembled device in the open state, according to an embodiment of the present invention. Device 10 is configured to grip a catheter, and is also herein termed grip 10. Grip 10 is comprised of three entities: a pair of ridged jaws 12, 14, and a resilient joint 16, herein assumed to comprise a spring and also referred to as spring 16. Jaws 12 and 14 are configured to interleave with each other in the assembled form of the grip, and are sized so that the assembled grip is conveniently grasped between the thumb and fingers of one hand of an operator of the grip. By way of example, ridged jaws 12 and 14 are also substantially similar in form, although this is not a necessity. In some embodiments the two jaws have identical geometric forms. Typically, jaws 12 and 14 are unitary pieces of plastic, which may conveniently made by a plastic forming method such as injection molding. In its assembled state, grip 10 has an approximately circular cross-section.

For simplicity, the following description of the ridged jaws is written for jaw 12, and except where otherwise noted the same description applies for jaw 14. To differentiate corresponding parts of the two jaws the letter A is added to the identifying numeral of jaw 14. Thus, jaw 12 comprises a holding portion 20, and jaw 14 comprises a holding portion 20A. Holding portions 20 and 20A are also termed exterior sides 20 and 20A of their respective jaws. Portions 20 and 20A may be used by an operator of the grip to manually grasp the grip using the fingers and thumb of one hand.

Exterior side 20 is bounded by a generally arcuate section 24, and ridges 28 and indentations 30 substantially traverse the complete width of the side. Apart from arcuate section 24, exterior side 20 is also bounded by a pair of generally linear elements 34, 36. A groove 40, shaped to accept a corresponding portion 42 of spring 16, is formed in an outer surface 44 of side 20.

Jaw 12 also comprises a leafed portion 50 which is attached to holding portion 20. Leafed portion 50 comprises a plurality of generally similar leaves 54, assumed herein by way of example to comprise five leaves 54, four of which have similar widths, and a fifth, outer, leaf being thicker than the other leaves. Where the leaves are not attached to holding portion 20, they are each bounded by a generally arcuate section 56, the arc of section 56 continuing the arc of arcuate section 24. The leaves are also bounded by two generally linear sections 60, 62. Ridges 28 and indentations 30 are formed in arcuate section 36. In addition, a passage 70 is formed in each of the leaves, the passage having a width somewhat greater than the diameter of a catheter to be held by grip 10. Passage 70 is formed in each of leaves 54 as a generally radial element, each passage extending approximately from the equivalent of a center 72 of a circle 73 defined by the arcs of sections 24 and 56, to the equivalent of an exit point 75 of the circle. At its termination at center 72, passage 70 is configured as two half-circles 74, 76, separated by a preset distance approximately equal to the width of the passage. Half-circles 74, 76 have equal diameters, corresponding to the diameter of a catheter to be grasped by grip 10. Half-circles 74A have a common central axis 77; half-circles 74 have a common central axis 79. Axes 77 and 79 are referred to further below.

Grip 10 is assembled by inserting ridged jaws 12 and 14 so that their leaves 54, 54A interleave, and so that spring portions 42, 42A of spring 16 respectively mate with grooves 40, 40A.

FIG. 2 and FIG. 3 schematically illustrate grip 10 after assembly, and when spring 16 has been compressed. The state of the grip in this case, caused by manual compression of the grip, is termed the compressed grip state. The compressed grip state is typically achieved by grasping exterior sides 20 and 20A with the fingers and thumb of one hand, and squeezing the fingers towards the thumb. Such a motion causes a relative rotation of jaws 12 and 14 about an axis 80 of spring 16. The rotation rotates linear elements 60A and 62A until they respectively meet linear elements 34 and 36. The rotation also rotates linear elements 60 and 62 until they respectively meet linear elements 34A and 36A.

In the compressed grip state passages 70 and 70A, and centers 72 and 72A, align with each other, so that in this state an operator of the grip is able to transfer a catheter to and from centers 72, 72A via passages 70, 70A. However in a region 78 (FIG. 3) corresponding to aligned exit points 75, 75A, in proximity to the circumferential termination of passages 70, 70A, ridges 28 and 28A, and indentations 30 and 30A, do not align.

Grip 10 may transfer from its compressed state to an uncompressed state by the grip operator relaxing his/her hold on portions 20 and 20A. The operator relaxing his grip causes jaws 12 and 14 to rotate around axis 80 in a direction opposite to the rotation direction to achieve the compressed state.

Figure 4:
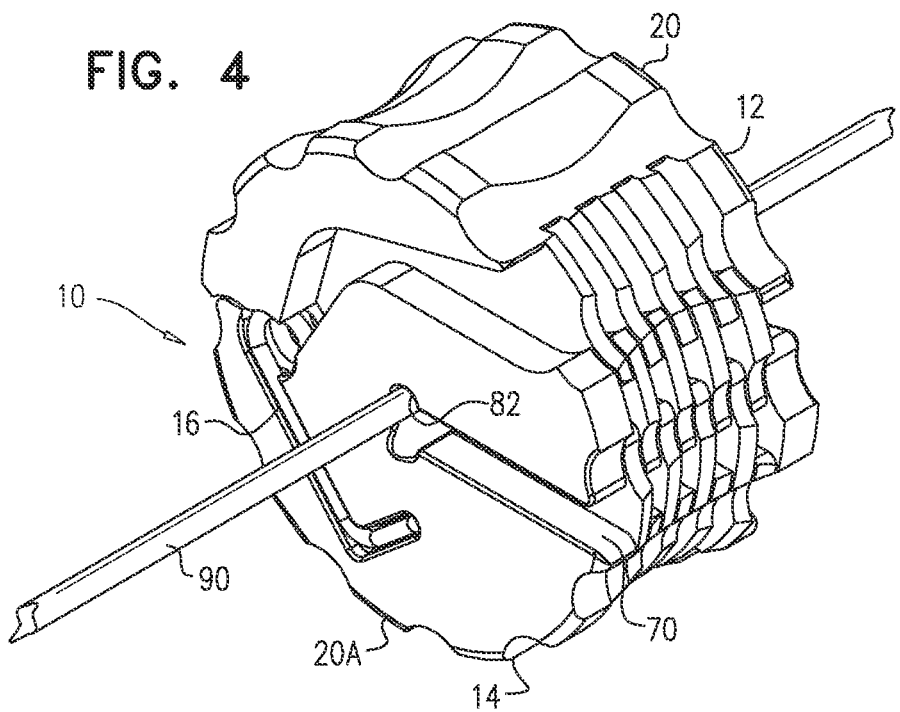
FIG. 4 is a schematic view of the catheter device in a closed state, according to an embodiment of the present invention.
Figure 5:
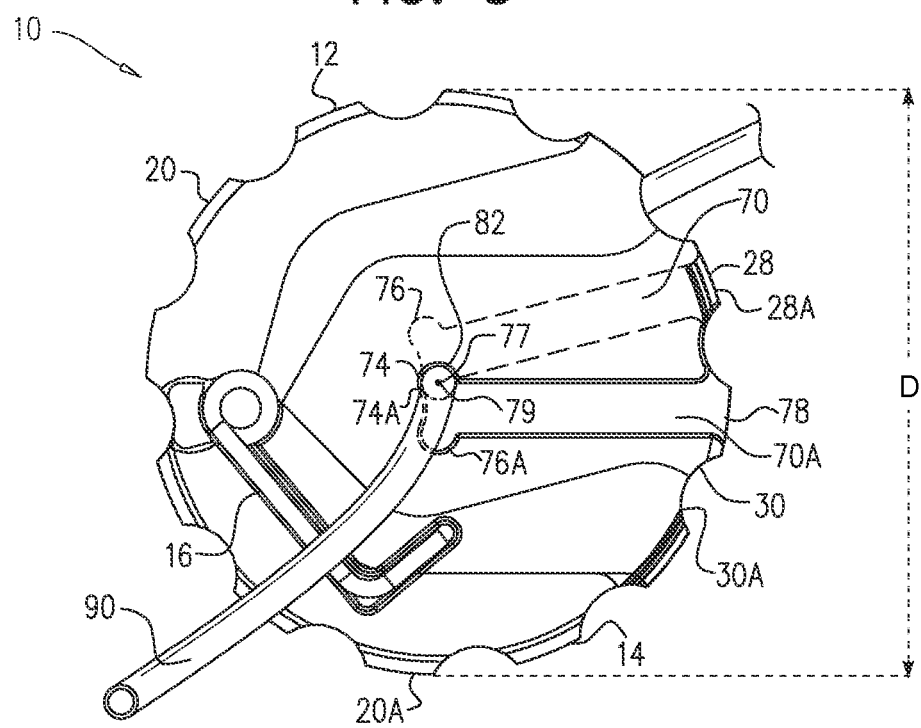
FIG. 5 is another schematic view of the catheter device in the closed state, according to an embodiment of the present invention.

FIGS. 4 and 5 are two schematic views of grip 10 in its uncompressed state, according to an embodiment of the present invention. In the uncompressed state passages 70 and 70A move out of alignment, as do sets of half-circles 74 and sets of half-circles 76A, and half-circles 74A and 76. However the rotation into its uncompressed state aligns the centers of half-circles 74A and half-circles 74, so that axes 77 and 79 align, and so that the two sets of half-circles form a cylindrical tube-like opening 82. If a catheter 90 has been placed within passages 70, 70A of grip 10 in its compressed state, then the catheter moves to opening 82 along aligned axes 77 and 79, and is grasped there by the grip, when the grip rotates to its uncompressed state. In addition, in contrast to the compressed state, in the uncompressed state ridges 28, 28A and indentations 30, 30A align in region 78.

By virtue of the external diameter of grip 10, it is significantly easier for a physician to rotate and/or translate catheter 90 grasped by grip 10, as compared to the physician attempting to rotate or translate the catheter by grasping the catheter directly. Typically, an external diameter D (FIG. 5) of a curved surface of grip 10, corresponding to exterior side 20 of jaw 12 and exterior side 20A of jaw 14, is configured to be at least 15 times the diameter of the catheter held by the grip. In some embodiments of the present invention, a number of grips, generally similar to grip 10 but having different external diameters, may be made available to the physician, enabling the physician to select a grip most suitable for manipulating the catheter. In an alternative embodiment, the external diameter of grip 10 may be custom-formed according to the requirement of a specific physician.

Figure 6A:
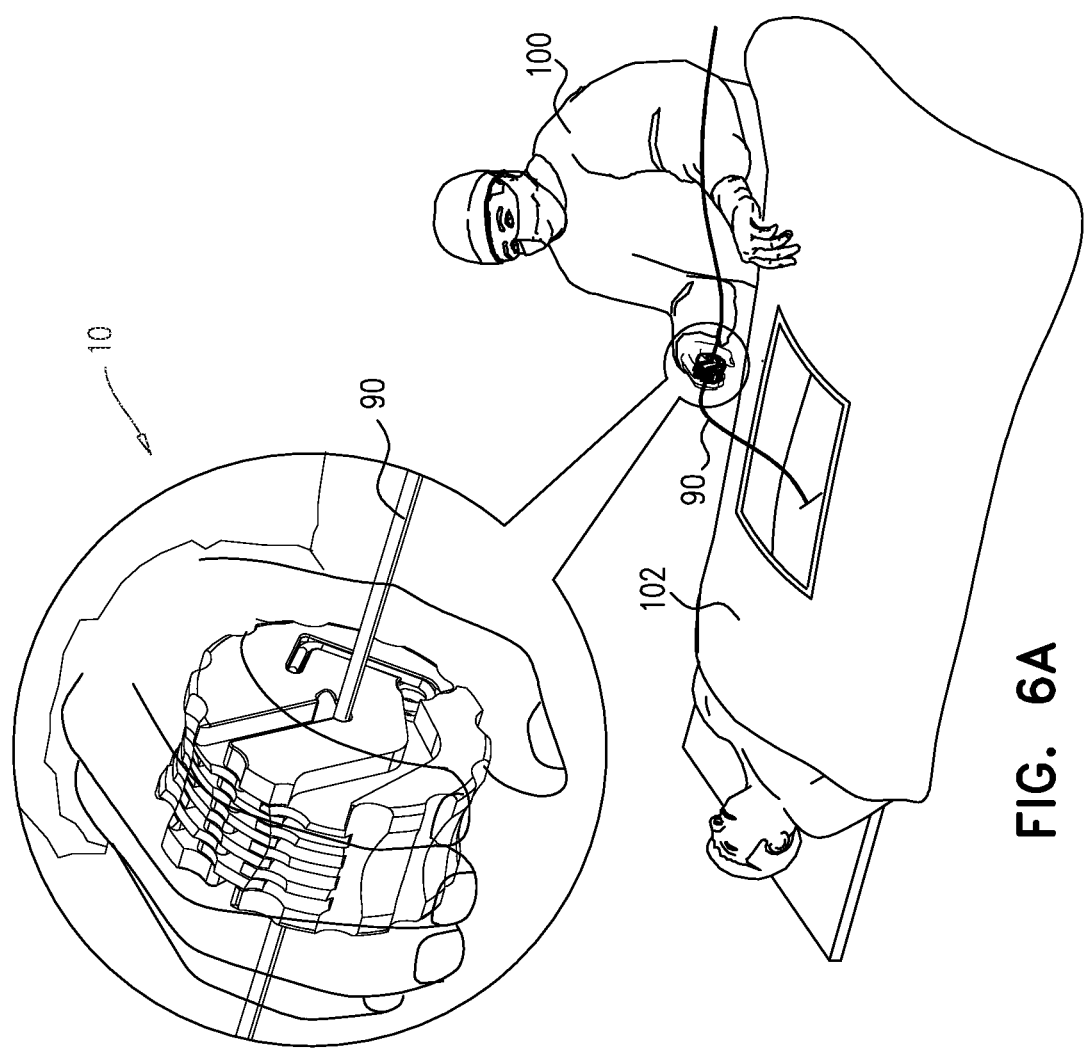
FIGS. 6A and 6B are schematic views of the grip in a closed state; according to embodiments of the present invention.
Figure 6B:
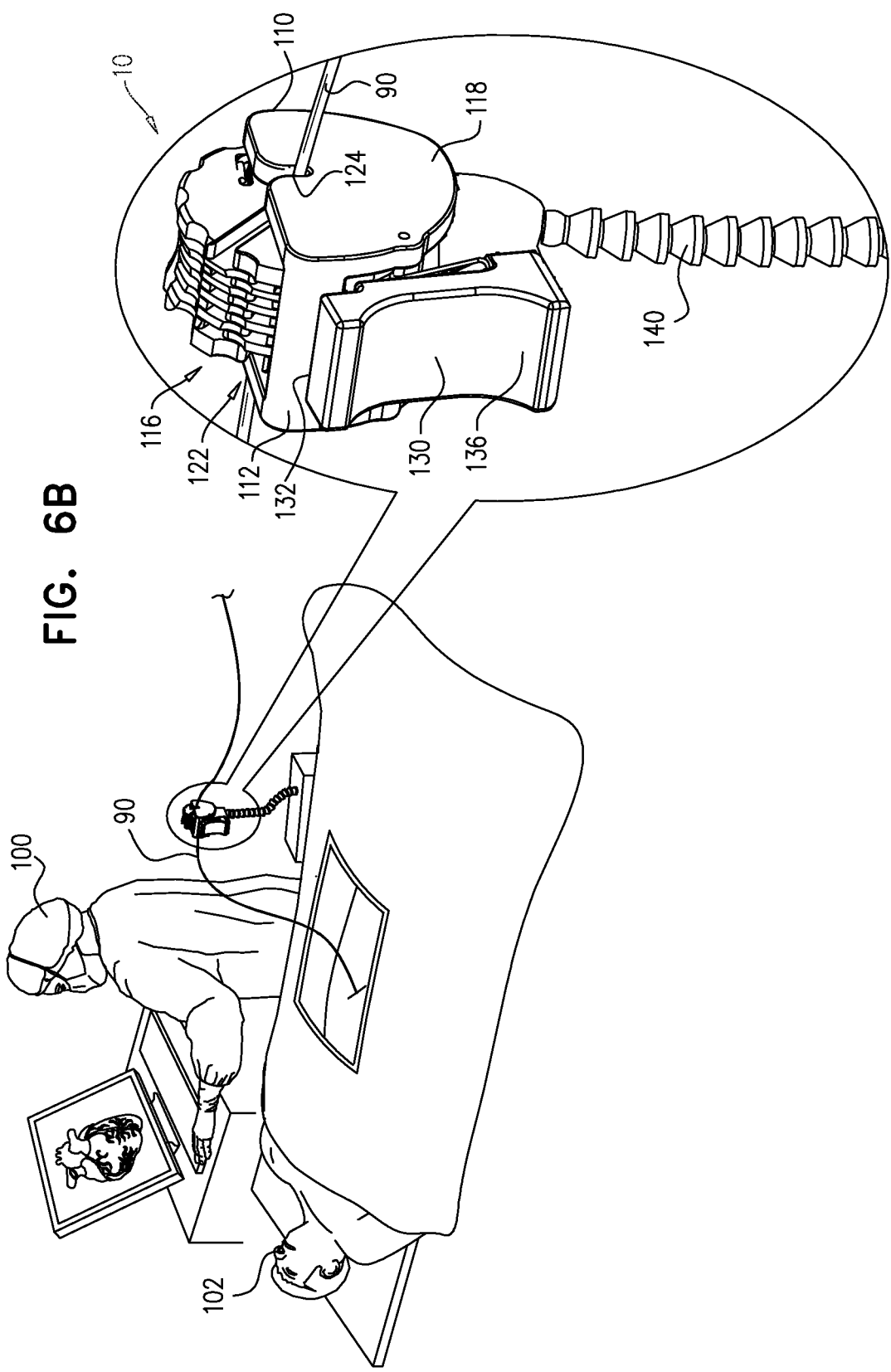

FIG. 6A is a schematic drawing of grip 10, in its uncompressed state, as it is held by a physician 100 during a medical procedure, and FIG. 6B is a schematic drawing of the grip mounted in a cradle during the procedure, according to embodiments of the present invention. A typical medical procedure where grip 10 may be used comprises an ablation procedure performed by physician 100 on a patient 102, although other medical procedures where the grip could be used will be apparent to those having ordinary skill in the art. During the procedure physician 100 inserts catheter 90 into the patient, and at any convenient time after an initial insertion the physician may grasp the catheter with grip 10. The grasping of the catheter by grip 10 is performed by inserting the catheter into passages 70, 70A while the physician compresses the grip to its compressed state, then relaxing the compression of the grip so that the grip returns to its uncompressed state.

Using grip 10 in its uncompressed state the physician manipulates the catheter into a desired position, as is illustrated in FIG. 6A. Once in position, the grip, with the grasped catheter may be placed in a cradle 110 as is illustrated in FIG. 6B. Cradle 110 comprises a generally U-shaped element 112 having an internal diameter approximately equal to the external diameter of grip 10. Two plane elements 116, 118, approximately semicircular in shape, close off the ends of element 112.

Plane elements 116, 118 respectively have narrow U-shaped openings 122, 124 formed in the elements. U-shaped openings 122, 124 are configured to allow catheter 90 to freely move in the openings, so that when grip 10, with its grasped catheter 90, is placed in the cradle, there is very little force exerted on the catheter by the cradle.

Cradle 110 comprises a spring-loaded stopper 130, which typically has a head 132 having a shape matching the shape of indentations 30 and 30A. Element 112 comprises an opening allowing head 132 to contact the periphery, i.e., sides 20, 20A, of grip jaws 12, 14. Stopper 130 also has a base 136 and the stopper may typically be operated by the operator pressing on base 136. A stopper-disengaged state occurs when the operator presses on base 136, so that head 132 does not engage with ridges 28, 28A or with indentations 30, 30A. A stopper-engaged state occurs when the operator releases the pressure on base 136, so that head 122 contacts ridges 28, 28A, or engages indentations 30, 30A. If the stopper head engages indentations 30, 30A, then it effectively locks grip 10, and catheter 90, in place. Thus, stopper 130 and grip 10 act as a pawl and ratchet combination.

By way of example the description above of stopper 130 assumes that the stopper is mounted on U-shaped element 112 of cradle 110. However, it will be understood that stopper 130 may be mounted on any other convenient element of the cradle such as on plane elements 116 or 118. If the stopper is mounted on an element other than U-shaped element 112, those having ordinary skill in the art will be able to adapt the above description for the operation of the stopper, mutatis mutandis, to accommodate changes that may be required for the operation. Such changes may include, but are not limited to, incorporating ridges and/or indentations, engadgeable by the stopper, in outer leaves 54 and/or 54A if the stopper is mounted on elements 116 or 118.

Cradle 100 may typically be mounted on an adjustable arm 140 which may be fixed at its base, or which may have its base adjustable, such as by mounting the base on a rail. The cradle mounting is configured so that the cradle may be conveniently fixedly positioned in any location selected by the physician. Once the grip is fixed in position, the physician has his/her hands free for other tasks.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. An assembly for gripping a catheter, the assembly comprising:
   a central axis;
   a first jaw body having:
      a first grip surface on a first exterior side of the first jaw body,
      a first opening extending through the first jaw body along an axis parallel to the central axis, and
      a first passage;
   a second jaw body having:
      a second grip surface on a second exterior side of the second jaw body,
      a second opening extending through the second jaw body along an axis parallel to the central axis, and
      a second passage; and
   a resilient joint;
   wherein, in an assembled state, the resilient joint connects the first jaw body to the second jaw body in such a way that the first and second openings are aligned with the central axis;
   wherein the first passage extends radially away from the first opening through the first jaw body to a first exit point on the first grip surface;
   wherein the second passage extends radially away from the second opening through the second jaw body to a second exit point on the second grip surface;
   wherein in a compressed state the first and second passages and the first and second exit points are mutually aligned, such that the catheter can be inserted through the first and second exit points along the first and second passages to the first and second openings; and
   wherein in an uncompressed state the first and second passages and the first and second exit points are no longer mutually aligned and a portion of the first opening and a portion of the second opening are in alignment to form a tube-like opening, the tube like opening aligned with the central axis and dimensioned to grip a catheter in alignment with the central axis when the catheter is arranged through the tube-like opening.

2. The assembly according to claim 1, wherein the first jaw body comprises a first plurality of first jaw leaves, and the second jaw body comprises a second plurality of second jaw leaves which interleave with the first jaw leaves.

3. The assembly according to claim 1, wherein the first and second jaw bodies have identical geometric forms.

4. The assembly according to claim 1, wherein the first grip surface comprises a first set of ridges and indentations, and the second grip surface comprises a second set of ridges and indentations.

5. The assembly according to claim 4, wherein the first set and the second set of ridges and indentations align in a region in proximity to the first exit point and the second exit point upon release of the manual compression.

6. The assembly according to claim 4, wherein the first jaw body, the second jaw body, and the resilient joint connecting the jaw bodies form a catheter grip, the device further comprising a cradle which is configured to receive the catheter grip.

7. The assembly according to claim 6, wherein the cradle comprises a pawl which is configured to engage with at least a first indentation selected from the first and second sets of indentations and ridges so as to lock the catheter grip in place in the cradle.

8. The device assembly to claim 1, wherein the catheter has a catheter diameter, and wherein release of the manual compression causes the first and second exterior sides to form a curved surface having a diameter at least 15 times greater than the catheter diameter.

9. The assembly according to claim 1, wherein each one of the first and second openings comprises first and second half-circles separated by a preset distance, the first half-circle of the first opening defining a first opening portion of the tube-like opening and the second half-circle of the second opening defining a second opening portion of the tube-like opening.

10. The assembly according to claim 9, wherein the preset distance is equal to the width of respective first and second passages.

11. The assembly according to claim 9, wherein the half-circles have equal diameters corresponding to the diameter of a catheter to be grasped by grip.

12. A method for gripping a catheter, comprising:
   providing an assembly comprising:
      a first jaw body having:
         a first grip surface on a first exterior side of the first jaw body,
         a first opening extending through the first jaw body along an axis parallel to the central axis, and
         a first passage extending radially away from the first opening;
      a second jaw body having:
         a second grip surface on a second exterior side of the second jaw body,
         a second opening extending through the second jaw body along an axis parallel to the central axis, and
         a second passage; and
      a resilient joint;
      wherein, in an assembled state, the resilient joint connects the first jaw body to the second jaw body in such a way that the first and second openings are aligned with the central axis;
      wherein the first passage extends radially away from the first opening through the first jaw body to a first exit point on the first grip surface;
      wherein the second passage extends radially away from the second opening through the second jaw body to a second exit point on the second grip surface;
   manually compressing the assembly to cause a relative rotation between the first and second jaw bodies that misaligns the first and second openings with respect to the central axis, and mutually aligns the first and second radial passages and the first and second exit points with each other;
   inserting a catheter through the first and second exit points and along the first and second radial passages to the first and second openings; and
   releasing the manual compression to cause the first and second jaw bodies to rotate so that the first and second passages are no longer mutually aligned and portions of the first and second openings are arranged to form a tube-like opening;
   wherein releasing the manual compression with the catheter located in the first and second openings causes the catheter to be gripped in alignment with the central axis by the tube-like opening.

13. The method according to claim 12, wherein the first jaw body comprises a first plurality of first jaw leaves, and the second jaw body comprises a second plurality of second jaw leaves which interleave with the first jaw leaves.

14. The method according to claim 12, wherein the first and second jaw bodies have identical geometric forms.

15. The method according to claim 12, wherein the first grip surface comprises a first set of ridges and indentations, and the second grip surface comprises a second set of ridges and indentations.

16. The method according to claim 15, wherein the first set and the second set of ridges and indentations align in a region in proximity to the first exit point and the second exit point upon release of the manual compression.

17. The method according to claim 15, wherein the first jaw body, the second jaw body and the resilient joint connecting the jaw bodies form a catheter grip, the method further comprising providing a cradle which is configured to receive the catheter grip.

18. The method according to claim 17, wherein the cradle comprises a pawl which is configured to engage with at least a first indentation selected from the first and second sets of indentations and ridges so as to lock the catheter grip in place in the cradle.

19. The method according to claim 12, wherein the catheter has a catheter diameter, and wherein release of the manual compression causes the first and second exterior sides to form a curved surface having a diameter at least 15 times greater than the catheter diameter.

20. The method according to claim 12, wherein each one of the first and second openings comprise first and second half-circles separated by a preset distance, the first half-circle of the first opening defining a first opening portion of the tube like opening and the second half-circle of the second opening defining a second opening portion of the tube like opening.

21. The method according to claim 20, wherein the preset distance is equal to the width of respective first and second passages.

22. The method according to claim 20, wherein the half-circles have equal diameters corresponding to the diameter of a catheter to be grasped by grip.

\* \* \* \* \*